United States Patent
Zhang et al.

(10) Patent No.: US 12,091,375 B2
(45) Date of Patent: Sep. 17, 2024

(54) PREPARATION METHOD FOR TRIPHENYLCHLOROMETHANE

(71) Applicants: Linhai Huanan Chemical Co., Ltd., Zhejiang (CN); Zhejiang Huahai Pharmaceutical Co., Ltd., Zhejiang (CN)

(72) Inventors: Lu Zhang, Zhejiang (CN); Guoliang Tu, Zhejiang (CN); Jianyue Xu, Zhejiang (CN); Heping Jin, Zhejiang (CN); Su Wang, Zhejiang (CN); Qi Hu, Zhejiang (CN); Sen Yang, Zhejiang (CN); Heng Liu, Zhejiang (CN)

(73) Assignees: Linhai Huanan Chemical Co., Ltd., Zhejiang (CN); Zhejiang Huahai Pharmaceutical Co., Ltd., Zhejiang (CN)

( * ) Notice: Subject to any disclaimer, the term of this patent is extended or adjusted under 35 U.S.C. 154(b) by 328 days.

(21) Appl. No.: 17/616,454

(22) PCT Filed: Jan. 6, 2020

(86) PCT No.: PCT/CN2020/070510
§ 371 (c)(1),
(2) Date: Dec. 3, 2021

(87) PCT Pub. No.: WO2020/244225
PCT Pub. Date: Dec. 10, 2020

(65) Prior Publication Data
US 2022/0234970 A1    Jul. 28, 2022

(30) Foreign Application Priority Data
Jun. 5, 2019   (CN) .......................... 201910486205.8

(51) Int. Cl.
*C07C 17/16*   (2006.01)
(52) U.S. Cl.
CPC .................................. *C07C 17/16* (2013.01)
(58) Field of Classification Search
None
See application file for complete search history.

(56) References Cited

FOREIGN PATENT DOCUMENTS

| CN | 102718624 A | 10/2012 |
| CN | 110204413 A | 9/2019 |

OTHER PUBLICATIONS

Flinn "Hydrochloric Acid 6M-12M", Dec. 3, 2018; pp. 1-3 (Year: 2018).*
Gardner, C. et al. "Mechanism of Methanolysis of Triphenyl Chloride in Benzene Solution", Dec. 3, 2018; pp. 1-3 (Year: 2018).*
Extended European Search Report of Corresponding EP Application 20818663.5 dated Jun. 28, 2022, all pages cite in its entirety.
Gomberg M., et al., On Triphenylmethyl.: [Twentieth Paper.], Journal of the American Chemical Society, 1911, pp. 531-549, 33(4).
Gomberg M., et al., Triphenylmethyl. XXX. Diphenyl-Beta-Naphthyl-Methyl and the Color of Free Radicals, Journal of the American Chemical Society, 1922, pp. 1810-1833, 44(8).
Clark, et al., A Systematic Study of the Preparation of Alkyl Chlorides from the Corresponding Alcohols, Transactions of the Royal Society of Canada, Jan. 1, 1929, pp. 77-89, vol. 23, Section III, Canada.
Efficient Preparation of Triphenylchloromethane from Trityl Alcohol (2002).
Preparation of Triphenylchloromethane (2018).
Selenium and Tellurium Tetrachlorides as Reagenis for the Conversion of Alcohols to Alkyl Chlorides and Tellurium Tetrachloride as a Lewis Acid Catalyst for Aromatic Alkylation; The Chemical Society of Japan(1986).
First Office Action of corresponding CN Application No. 202080031514.7 issued on Feb. 22, 2023, all enclosed pages cited.

* cited by examiner

*Primary Examiner* — Medhanit W Bahta
(74) *Attorney, Agent, or Firm* — Burr & Forman LLP

(57)   ABSTRACT

Disclosed is a preparation method for triphenylchloromethane, comprising the following steps: adding hydrochloric acid or a mixture of hydrochloric acid and Lewis acid to a mixture of triphenylmethanol and an organic solvent; stirring for reaction; removing the water layer after the completion of reaction to obtain an organic solution containing triphenylchloromethane. In the method, the conversion rate of triphenylmethanol is almost quantitative to be above 99%, and the content of triphenylchloromethane in the product obtained is above 99%. The operation is simple, and no waste gas is generated. Therefore, the method is environmentally friendly and suitable for industrialized production and can achieve better economic benefits.

19 Claims, 2 Drawing Sheets

PREPARATION METHOD FOR TRIPHENYLCHLOROMETHANE

The present application claims the priority of the Chinese Patent Application No. 201910486205.8, with the title of "RECYCLING AND REUSE PROCESS FOR PREPARING TRIPHENYLCHLOROMETHANE", filed on Jun. 5, 2019 before the China National Intellectual Property Administration, which is incorporated herein by reference in its entirety.

TECHNICAL FIELD

The present application belongs to the technical field of medicine, and particularly relates to a method for preparing triphenylchloromethane.

BACKGROUND OF THE INVENTION

Triphenylchloromethane is a white crystal, insoluble in water, easily soluble in benzene, carbon disulfide, petroleum ether, n-hexane, slightly soluble in alcohols and ethers, and is converted into triphenylmethanol after absorbing water. Triphenylchloromethane is one of the basic organic raw materials commonly used in the field of pharmaceutical and chemical industry. In the process of organic chemical industry and drug synthesis, since triphenylmethyl and similar protective groups thereof have the characteristics of being easy to introduce and remove under mild conditions, good stability and large steric hindrance, they have been developed into one of the most commonly used amino or hydroxyl protecting groups, especially in the selective protection of polyhydroxy compounds.

Triphenylchloromethane is a raw material for preparing N-triphenylmethyl-5-[4'-methylbiphenyl-2-yl]tetrazolium (Formula I), in which N-triphenylmethyl-5-[4'-Methylbiphenyl-2-yl]tetrazolium (Formula I) is an important intermediate for preparing Olmesartan, Losartan, Valsartan, Irbesartan and Candesartan, and its structural formula is as follows:

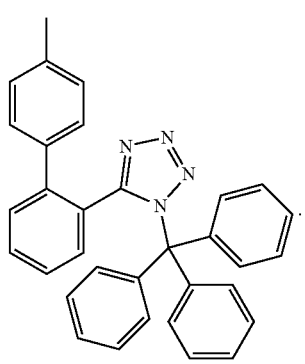

Formula I

N-triphenylmethyl-5-[4'-methylbiphenyl-2-yl]tetrazolium (Formula I) is prepared by the reaction of 4'-methylbiphenyltetrazolium as a raw material with triphenylchloromethane, and the synthetic route is as follows:

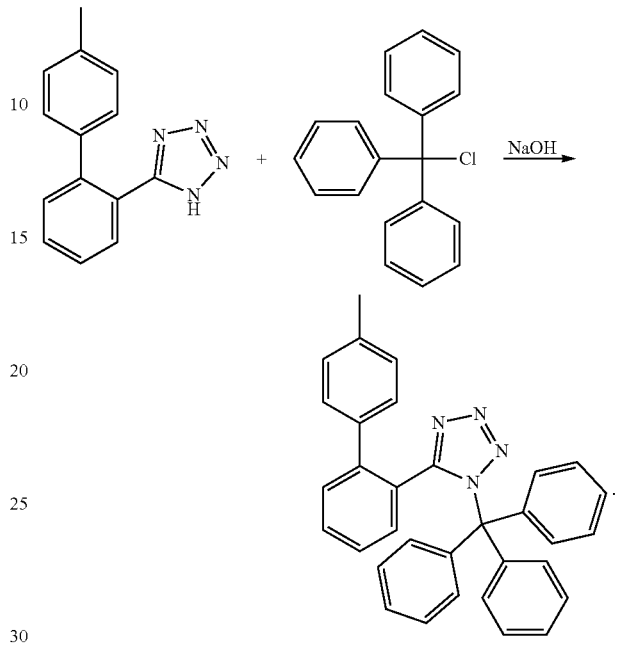

In the synthesizing process of most antihypertensive drugs of the "sartan" family, triphenylmethyl is a protecting group of the amine group. After the protection is completed, it is removed from the main structure to obtain the target sartan compounds and triphenylmethanol. Triphenylmethyl is easy to remove with acid. For example, it can be removed smoothly with HOAc or 50% or 75% HOAc aqueous solution at 30° C. or by refluxing for a few minutes. Tiphenylmethyl can be also removed by using HCl/MeOH, HCl/CHCl$_3$, HBr/HOAc, TFA and the like conveniently to generate triphenylmethanol. The reuse of triphenylmethanol has a huge impact on the environment and economic benefits. Therefore, the development of an efficient and green synthesis process for preparing triphenylchloromethane by using recycled triphenylmethanol has high economic and environmental value.

Regarding preparing triphenylchloromethane by using triphenylmethanol, the commonly used industrialized method at present is reacting triphenylmethanol with thionyl chloride. This method has following problems in the actual application process.

1. A large amount of waste gas including sulfur dioxide and hydrogen chloride is produced during the production process, the equipment is corroded seriously, and the operating environment is harsh.

2. A lot of side reactions occur, the yield is low, and it is easy to produce tar-like substances, difficult for post-processing, which limits large-scale industrial production.

Therefore, there is an urgent need to develop a method for preparing triphenylchloromethane, which is easy to industrialize and environmentally friendly.

SUMMARY OF THE INVENTION

The present application provides a simple and efficient method for preparing triphenylchloromethane by using triphenylmethanol, so as to reduce pollution, simplify operation, improve yield, and reduce costs, and finally make it suitable for the continuous and large-scale recycling of triphenylmethyl as a protective group.

Triphenylmethanol can react with hydrogen chloride to produce triphenylchloromethane, and at the same time, triphenylmethane can easily produce triphenylmethanol and hydrogen chloride when reacting with water. This is a reversible reaction.

The inventors of the present application find that triphenylmethanol and triphenylchloromethane are more soluble in organic solvents. Based on this discovery, after adding concentrated hydrochloric acid to the mixture of triphenylmethanol and organic solvents, the organic phase containing triphenylmethanol can be layered with aqueous phase, and there is almost no water in the organic phase; hydrogen chloride can be released from the concentrated hydrochloric acid in the aqueous phase, which can continue to diffuse into the organic phase. Thus, the reversible reaction moves in the positive direction, and the hydrolysis reaction hardly proceeds. Lewis acids such as calcium chloride can increase the release of hydrogen chloride, which is more beneficial for proceeding reaction in the positive direction.

Based on the above discovery, the present application provides a method for preparing triphenylchloromethane, comprising the following steps:
  adding hydrochloric acid or a mixture of hydrochloric acid and Lewis acid to a mixture of triphenylmethanol and an organic solvent, reacting at 5-35° C. under stirring, separating a product from an organic phase after the reaction is completed to obtain a solid containing triphenylchloromethane, and preferably, recrystallizing the solid; and
  obtaining triphenylchloromethane after drying;
  wherein the reaction scheme is as follows:

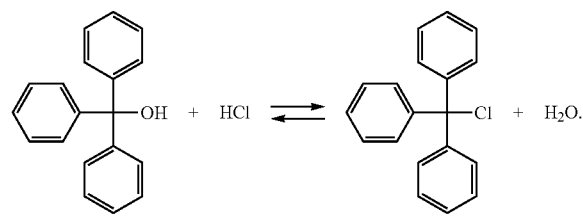 [SMILES: OC(c1ccccc1)(c1ccccc1)c1ccccc1 ; Cl ; ClC(c1ccccc1)(c1ccccc1)c1ccccc1 ; "H2O."]

In some embodiments of the present application, Lewis acid is at least one of anhydrous calcium chloride, anhydrous aluminum chloride, anhydrous ferric chloride and anhydrous zinc chloride, preferably anhydrous calcium chloride.

In some embodiments of the present application, the molar concentration of hydrochloric acid is 1-12 mol/L, preferably 5-12 mol/L, and more preferably 10-12 mol/L.

In some embodiments of the present application, the molar ratio of hydrochloric acid to triphenylmethanol is 15:1-1.5:1, preferably 10:1-1.5:1.

In some embodiments of the present application, the molar ratio of hydrochloric acid to Lewis acid is 1:1-1:0.01, preferably 1:1-1:0.1.

In some embodiments of the present application, the reaction temperature is 15-25° C.

In some embodiments of the present application, the reaction time is 0.5 to 10 hours, preferably 1 to 5 hours.

In some embodiments of the present application, the organic solvent is at least one of tetrahydrofuran, 2-methyltetrahydrofuran, carbon disulfide, nitromethane, acetonitrile, chlorinated alkane, aromatic hydrocarbon, an ether solvent, an ester solvent and a ketone solvent.

In some embodiments of the present application, the chlorinated alkane is at least one of dichloromethane, chloroform, carbon tetrachloride, 1,1-dichloroethane, 1,2-dichloroethane, 1,1,1-trichloroethane, 1,1,2-trichloroethane and 1,1,2,2-tetrachloroethane, preferably dichloromethane.

The aromatic hydrocarbon is at least one of toluene, chlorobenzene and nitrobenzene, preferably toluene.

The ether solvent is at least one of ethyl ether, propyl ether, isopropyl ether and butyl ether, preferably isopropyl ether.

The ester solvent is at least one of methyl acetate, ethyl acetate, propyl acetate, butyl acetate, isopropyl acetate, isobutyl acetate, pentyl acetate and isoamyl acetate, preferably ethyl acetate.

The ketone solvent is at least one of acetone, butanone and methyl isobutyl ketone, preferably methyl isobutyl ketone.

In some embodiments of the present application, a solvent for recrystallizing is at least one of petroleum ether, toluene, cyclohexane, n-hexane, n-heptane, ethyl acetate, acetone and methyl isobutyl ketone; preferably at least one of cyclohexane, n-heptane and toluene.

In some embodiments of the present application, the drying is preferably a vacuum drying; the drying temperature is preferably 40-60° C.; and the drying time is preferably 1-6 hours.

The terms used in the present application are generally those commonly used by those skilled in the art. If they are inconsistent with the commonly used terms, the terms should be understood by the definition of the present application.

In the present application, "chlorinated alkane" refers to an alkane containing 1-8 carbon atoms and at least one chlorine atom. Examples of chlorinated alkane include but not limited to methyl chloride, chloroform, carbon tetrachloride, 1,1-dichloroethane, 1,2-dichloroethane, 1,1,1-trichloroethane, 1,1,2-trichloroethane, 1,1,2,2-tetrachloroethane and the like.

In the present application, "aromatic hydrocarbon" refers to benzene or benzene containing at least one substituent; the substituent may be methyl, nitro, amino, chlorine, bromine, and the like. Examples of aromatic hydrocarbon include but not limited to toluene, chlorobenzene, nitrobenzene and the like.

In the present application, "an ether solvent" refers to an ether containing 1-8 carbon atoms. Examples of the ether solvent include but not limited to ethyl ether, propyl ether, isopropyl ether, butyl ether and the like.

In the present application, "an ester solvent" refers to an ester containing 1-8 carbon atoms. Examples of the ester solvent include but not limited to methyl acetate, ethyl acetate, propyl acetate, butyl acetate, isopropyl acetate, isobutyl acetate, pentyl acetate and isoamyl acetate.

In the present application, "a ketone solvent" refers to a ketone containing 1-8 carbon atoms. Examples of the ketone solvent include but not limited to acetone, butanone, and methyl isobutyl ketone.

The present application can achieve following beneficial effects.

1. The method for preparing triphenylchloromethane of the present application is carried out by using hydrochloric acid or a mixture of hydrochloric acid and Lewis acid, which is simple to operate, without the production of waste gas, environmentally friendly, suitable for industrial production, and has good economic benefits.

2. In the preparation method of the present application, the conversion rate of triphenylmethanol is almost constant, and the content of triphenylchloromethane in the resulting product is more than 99%.

3. The process equipment of the present application is simple, without using a complicated tail gas absorption system, and only one reactor is needed in the original workshop to realize the recycle of triphenylchloromethane.

Therefore, the present application has developed a method for preparing triphenylchloromethane with convenient source of raw materials, low price, simple production process, and basically no pollution, which is beneficial to industrial production.

DESCRIPTION OF THE DRAWINGS

In order to illustrate the technical solutions of the examples of the present application and the prior arts more clearly, the drawings for the examples and the prior arts are briefly described as follow. Obviously, the drawings in the following description are merely some examples of the present invention. For those of skilled in the art, other drawings can be obtained based on these drawings without creative efforts.

DETAILED DESCRIPTION OF THE INVENTION

Preparation of Triphenylchloromethane

Figure 1:
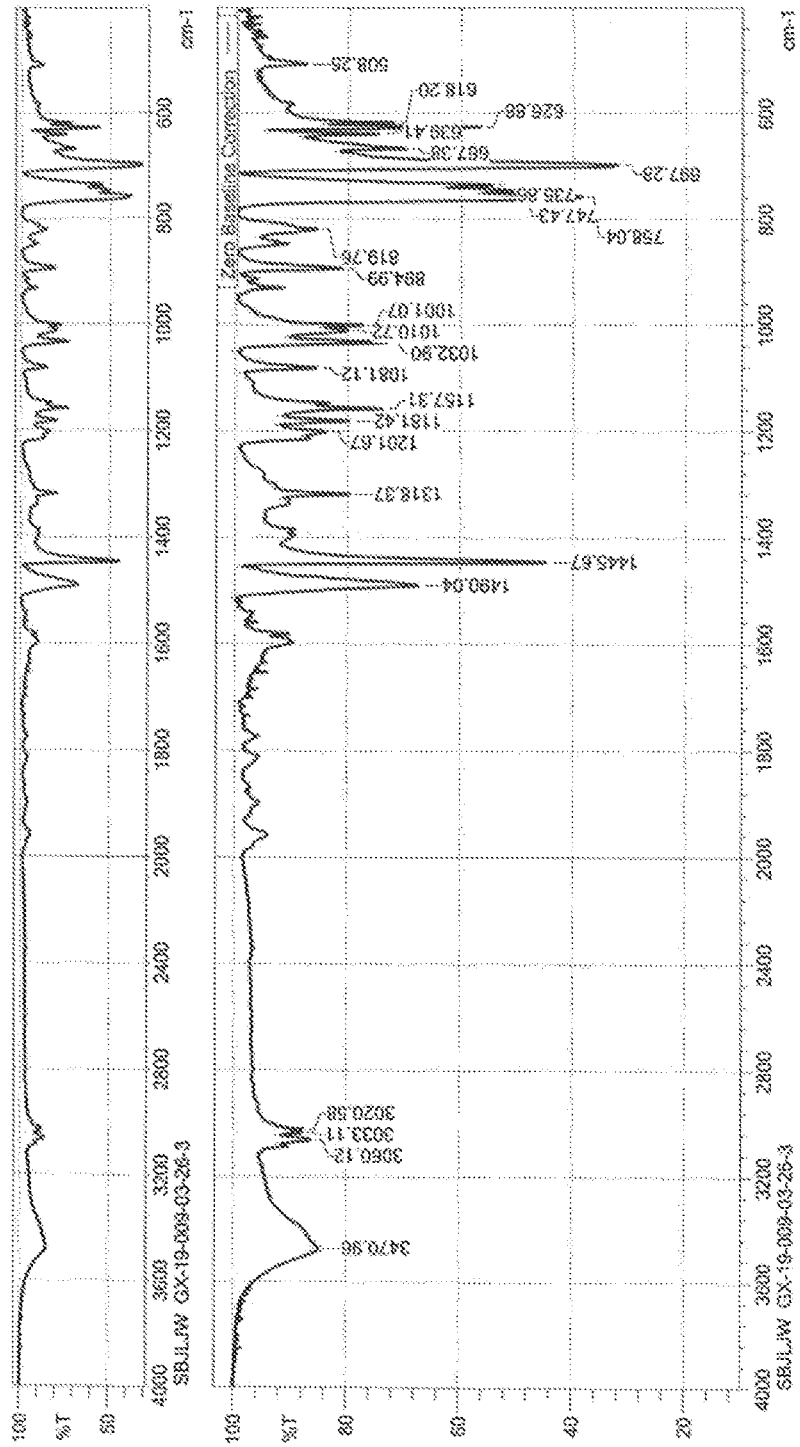
FIG. 1 is the infrared absorption spectrum of triphenylchloromethane standard.

The present application provides a method for preparing triphenylchloromethane, which comprises adding hydrochloric acid or a mixture of hydrochloric acid and Lewis acid to a mixture of triphenylmethanol and an organic solvent, reacting at 5-35° C. under stirring, separating a product from an organic phase after the reaction is completed to obtain a solid containing triphenylchloromethane, and preferably, recrystallizing the solid; obtaining triphenylchloromethane after drying; wherein the reaction scheme is as follows:

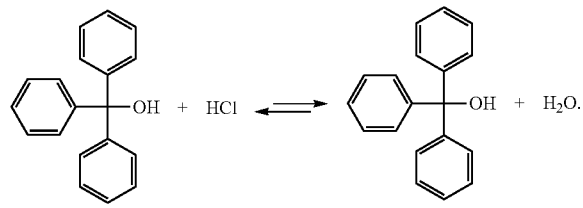 [SMILES: OC(c1ccccc1)(c1ccccc1)c1ccccc1 ; Cl ; OC(c1ccccc1)(c1ccccc1)c1ccccc1]

During the preparation process, since the organic solvent is not miscible with the water contained in the hydrochloric acid, after the reaction is completed, the organic phase and the aqueous phase can be layered by standing still. After the organic phase is obtained by separation, a solid containing triphenylchloromethane can be obtained by removing the organic solvent via conventional separation methods such as organic solvent evaporating. Further, the obtained solid can be recrystallized to increase the purity, improve the crystal form, and decolorization.

In some embodiments of the present application, Lewis acid is at least one of anhydrous calcium chloride, anhydrous aluminum chloride, anhydrous ferric trichloride, and anhydrous zinc chloride, preferably anhydrous calcium chloride.

In some embodiments of the present application, the molar concentration of hydrochloric acid is 1-12 mol/L, preferably 5-12 mol/L, and more preferably 10-12 mol/L.

The inventors of the present application unexpectedly discovered that Lewis acid can increase the release of hydrogen chloride and is more beneficial to the progress of the reaction. In addition, adding Lewis acid can reduce the concentration of hydrochloric acid used. Exemplarily, after adding Lewis acid, 1-8 mol/L, for example, 3-6 mol/L hydrochloric acid can be used for the reaction; whereas without adding Lewis acid, the concentration of hydrochloric acid of 8-12 mol/L, for example, 10-12 mol/L, will be more beneficial to the progress of the reaction.

In some embodiments of the present application, the molar ratio of hydrochloric acid to triphenylmethanol is 15:1-1.5:1, preferably 10:1-1.5:1.

In some embodiments of the present application, the molar ratio of hydrochloric acid to Lewis acid is 1:1-1:0.01, preferably 1:1-1:0.1.

By limiting the ratio of hydrochloric acid, triphenylmethanol, and Lewis acid to the above ranges, the yield of the obtained triphenylchloromethane is high, reaching 90% or more.

In some embodiments of the present application, the reaction temperature is 15-25° C.

In some embodiments of the present application, the reaction time is 0.5 to 10 hours, preferably 1 to 5 hours.

The method of the present application can prepare triphenylchloromethane at a relatively mild temperature, has low energy consumption, and is more suitable for industrial production.

In some embodiments of the present application, the organic solvent is at least one of tetrahydrofuran, 2-methyltetrahydrofuran, carbon disulfide, nitromethane, acetonitrile, chlorinated alkane, aromatic hydrocarbon, an ether solvent, an ester solvent and a ketone solvent.

In some embodiments of the present application, the chlorinated alkane is at least one of dichloromethane, chloroform, carbon tetrachloride, 1,1-dichloroethane, 1,2-dichloroethane, 1,1,1-trichloroethane, 1,1,2-trichloroethane and 1,1,2,2-tetrachloroethane, preferably dichloromethane.

The aromatic hydrocarbon is at least one of toluene, chlorobenzene and nitrobenzene, preferably toluene.

The ether solvent is at least one of ethyl ether, propyl ether, isopropyl ether and butyl ether, preferably isopropyl ether.

The ester solvent is at least one of methyl acetate, ethyl acetate, propyl acetate, butyl acetate, isopropyl acetate, isobutyl acetate, pentyl acetate and isoamyl acetate, preferably ethyl acetate.

The ketone solvent is at least one of acetone, butanone and methyl isobutyl ketone, preferably methyl isobutyl ketone.

The mixture of triphenylmethanol and organic solvent in the present application can be collected and recovered from the synthesis process of antihypertensive drugs of the "sartan" family. When triphenylchloromethane is prepared by using triphenylmethanol, the higher the purity of triphenylmethanol in the recovered mixed solution is, the higher the purity of the solid containing triphenylchloromethane obtained; when the purity of triphenylmethanol in the recovered mixed solution is relatively low, the purity of triphenylchloromethane can be further improved by recrystallizing.

In some embodiments of the present application, a solvent for recrystallizing is at least one of petroleum ether, toluene, cyclohexane, n-hexane, n-heptane, ethyl acetate, acetone and methyl isobutyl ketone; preferably at least one of cyclohexane, n-heptane and toluene.

In some embodiments of the present application, the drying is preferably a vacuum drying; the drying temperature is preferably 40-60° C.; and the drying time is preferably 1-6 hours.

In order to make the technical problems to be solved by the present application and the technical solutions and beneficial effects of the present application clearer, the present application will be further described below in combination with specific examples. In the following examples, unless otherwise specified, the specific conditions of the test method are usually implemented in accordance with conventional conditions or conditions recommended by the manufacturer; the raw materials and reagents are all commercially obtained or prepared by using public information.

Synthesis of Triphenylchloromethane

Example 1

500 mL of triphenylmethanol in toluene (containing 50 g of triphenylmethanol with a purity of 98% or more) was recovered, added with 50 mL of 12 mol/L concentrated hydrochloric acid, and the mixture was stirred at 25° C. for 5 h. After standing for 0.5 h, the aqueous layer was separated. The organic phase was concentrated to dryness without toluene by controlling the vacuum degree and the temperature for concentration <30° C. A solid containing triphenylchloromethane was obtained. The temperature was increased to 60° C. and the drying was continued for 5 h. The product was weighed to obtain 50.4 g of triphenylchloromethane, with a yield of about 94.1%, and a content of 99.0%.

Figure 2:
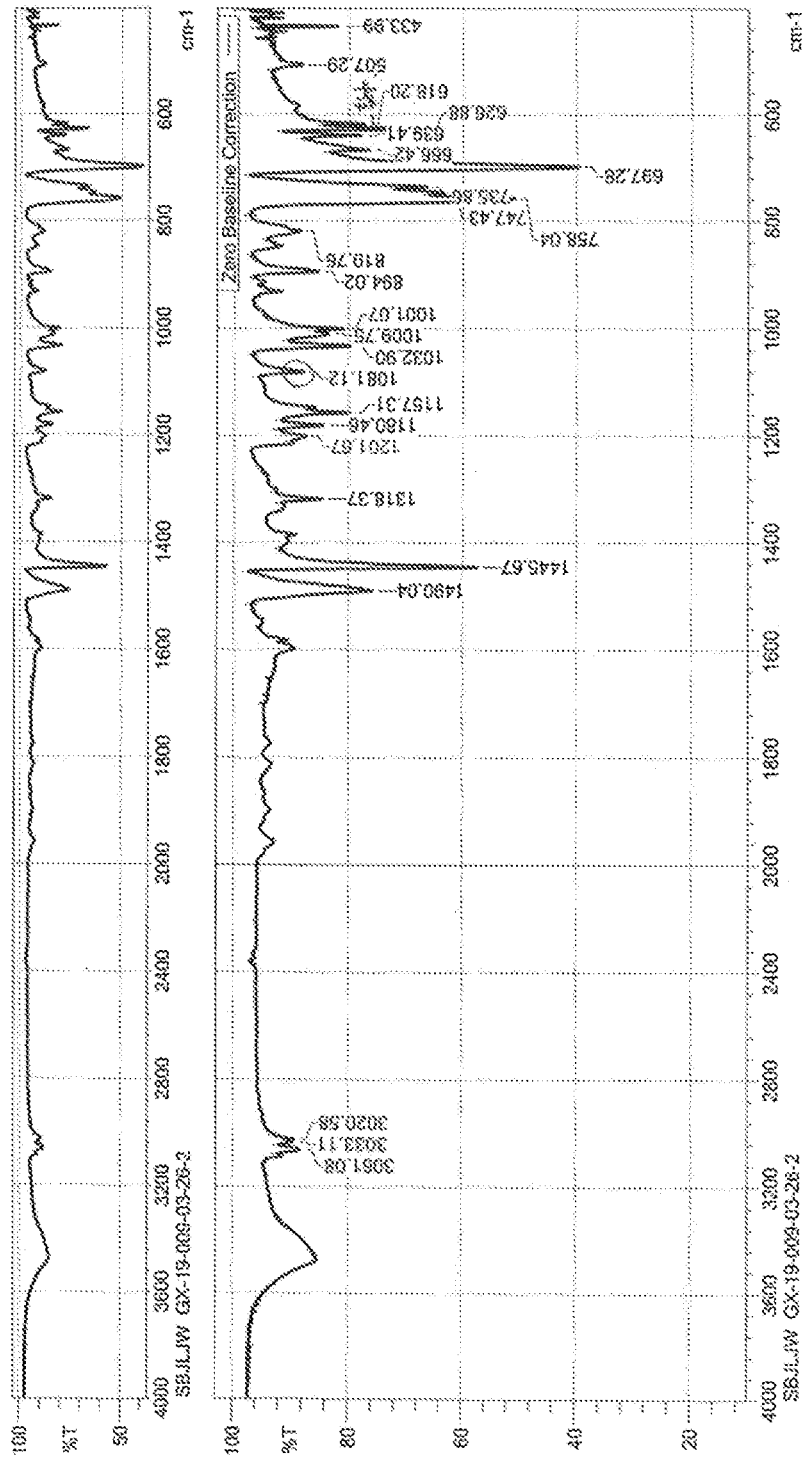
FIG. 2 is the infrared absorption spectrum of triphenylchloromethane prepared in Example 1.

The Fourier Transform Infrared Spectrometer (FT-IR) (Model:Nicolet 360) produced by Nicolet Company, United States was used for the infrared characterization of triphenylchloromethane standard and the triphenylchloromethane prepared in Example 1 (using KBr pellet, scanning at room temperature, the test range is 4000-400 cm$^{-1}$). The infrared spectrum of the triphenylchloromethane prepared in Example 1 was shown in FIG. 2, which was identical to that of the triphenylchloromethane standard shown in FIG. 1; and it was determined that the synthesized triphenylchloromethane was the target product.

Example 2

500 mL of triphenylmethanol in toluene (containing 50 g of triphenylmethanol with a purity of 98% or more) was recovered, added with 60 mL of 10 mol/L concentrated hydrochloric acid, and the mixture was stirred at 15° C. for 5 h. After standing for 0.5 h, the aqueous layer was separated. The organic phase was concentrated to dryness without toluene by controlling the vacuum degree and the temperature for concentration <30° C. A solid containing triphenylchloromethane was obtained. The temperature was increased to 60° C. and the drying was continued for 5 h. The product was weighed to obtain 50.4 g of triphenylchloromethane, with a yield of about 94.1%, and a content of 99.0%.

Example 3

500 mL of triphenylmethanol in toluene (containing 50 g of triphenylmethanol with a purity of 98% or more) was recovered, added with 100 mL of 6 mol/L concentrated hydrochloric acid and 5 g of calcium chloride, and the mixture was stirred at 25° C. for 5 h. After standing for 0.5 h, the aqueous layer was separated. The organic phase was concentrated to dryness without toluene by controlling the vacuum degree and the temperature for concentration <30° C. A solid containing triphenylchloromethane was obtained. The temperature was increased to 60° C. and the drying was continued for 5 h. The product was weighed to obtain 51.4 g of triphenylchloromethane, with a yield of about 96.0%, and a content of 99.3%.

Example 4

500 mL of triphenylmethanol in toluene (containing 50 g of triphenylmethanol with a purity of 98% or more) was recovered, added with 120 mL of 5 mol/L concentrated hydrochloric acid and 6 g of anhydrous ferric chloride, and the mixture was stirred at 35° C. for 2 h. After standing for 0.5 h, the aqueous layer was separated. The organic phase was concentrated to dryness without toluene by controlling the vacuum degree and the temperature for concentration <30° C. A solid containing triphenylchloromethane was obtained. The temperature was increased to 60° C. and the drying was continued for 5 h. The product was weighed to obtain 51.4 g of triphenylchloromethane, with a yield of about 96.0%, and a content of 99.3%.

Example 5

500 mL of triphenylmethanol in toluene (containing 50 g of triphenylmethanol with a purity of 98% or more) was recovered, added with 200 mL of 3 mol/L concentrated hydrochloric acid and 6 g of anhydrous aluminium chloride, and the mixture was stirred at 5° C. for 10 h. After standing for 0.5 h, the aqueous layer was separated. The organic phase was concentrated to dryness without toluene by controlling the vacuum degree and the temperature for concentration <30° C. A solid containing triphenylchloromethane was obtained. The temperature was increased to 60° C. and the drying was continued for 5 h. The product was weighed to obtain 51.4 g of triphenylchloromethane, with a yield of about 96.0%, and a content of 99.3%.

Example 6

500 mL of triphenylmethanol in methyl isobutyl ketone (containing 50 g of triphenylmethanol with a purity of 98% or more) was recovered, added with 75 mL of 8 mol/L concentrated hydrochloric acid and 5 g of calcium chloride, and the mixture was stirred at 25° C. for 5 h. After standing for 0.5 h, the aqueous layer was separated. The organic phase was concentrated to dryness without isobutyl ketone by controlling the vacuum degree and the temperature for concentration <30° C. A solid containing triphenylchloromethane was obtained. The temperature was increased to 60° C. and the drying was continued for 6 h. The product was weighed to obtain 51.4 g of triphenylchloromethane, with a yield of about 96.0%, and a content of 99.0%.

Example 7

500 mL of triphenylmethanol in dichloromethane (containing 50 g of triphenylmethanol with a purity of 98% or more) was recovered, added with 50 mL of 12 mol/L concentrated hydrochloric acid and 5 g of calcium chloride, and the mixture was stirred at 25° C. for 5 h. After standing for 0.5 h, the aqueous layer was separated. The organic phase was concentrated to dryness without dichloromethane by controlling the vacuum degree and the temperature for concentration <30° C. A solid containing triphenylchloromethane was obtained. The temperature was increased to 60° C. and the drying was continued for 5 h. The product was weighed to obtain 51.4 g of triphenylchloromethane, with a yield of about 95.0%, and a content of 99.1%.

Example 8

500 mL of triphenylmethanol in toluene (containing 50 g of triphenylmethanol with a purity of 98% or more) was recovered, added with 30 mL of 12 mol/L concentrated hydrochloric acid and 5 g of calcium chloride, and the mixture was stirred at 25° C. for 10 h. After standing for 0.5 h, the aqueous layer was separated. The organic phase was concentrated to dryness without toluene by controlling the vacuum degree and the temperature for concentration <30° C. A solid containing triphenylchloromethane was obtained. The temperature was increased to 60° C. and the drying was continued for 5 h. The product was weighed to obtain 51.3 g of triphenylchloromethane, with a yield of about 95.8%, and a content of 99%.

Example 9

500 mL of triphenylmethanol in toluene (containing 50 g of triphenylmethanol with a purity of 94.7%) was recovered, added with 100 mL of 6 mol/L concentrated hydrochloric acid and 5 g of calcium chloride, and the mixture was stirred at 25° C. for 5 h. After standing for 0.5 h, the aqueous layer was separated. The organic phase was concentrated to dryness without toluene by controlling the vacuum degree and the temperature for concentration <30° C. A solid containing triphenylchloromethane was obtained. After the solid was recrystallized with 320 mL petroleum ether, the temperature was increased to 60° C. and the drying was continued for 5 h. The product was weighed to obtain 51.3 g of triphenylchloromethane, with a yield of about 92.7%, and a content of 99.0%.

Example 10

500 mL of triphenylmethanol in dichloromethane (containing 50 g of triphenylmethanol with a purity of 95.0% or more) was recovered, added with 50 mL of 12 mol/L concentrated hydrochloric acid, 50 mL of water and 5 g of calcium chloride, and the mixture was stirred at 25° C. for 3 h. After standing for 0.5 h, the aqueous layer was separated. The organic phase was concentrated to dryness without dichloromethane by controlling the vacuum degree and the temperature for concentration <30° C. A solid containing triphenylchloromethane was obtained. The temperature was increased to 60° C. and drying was continued for 5 h. The product was weighed to obtain 51.3 g of triphenylchloromethane, with a yield of about 95.8%, and a content of 99.5%.

Example 11

500 mL of triphenylmethanol in toluene (containing 50 g of triphenylmethanol with a purity of 96.0% or more) was recovered, added with 50 mL of 12 mol/L concentrated hydrochloric acid, 50 mL of water, and 5 g of calcium chloride, and the mixture was stirred at 25° C. for 3 h. After standing for 5 h, the aqueous layer was separated. After weighing, 451.1 g of triphenylchloromethane in toluene solution was obtained, with a yield of about 96%, and a content of 11.4%. The triphenylchloromethane in toluene solution can be directly used for the next reaction.

Synthesis of N-triphenylmethyl-5-[4'-methylbiphenyl-2-yl]tetrazolium

Example 12

30.7 g of triphenylchloromethane prepared in Example 1 was dissolved in 50 mL of toluene;
23.6 g of biphenyltetrazolium was dissolved in 100 mL of toluene, and added with sodium hydroxide aqueous solution. The mixture was stirred for 1 h, and added with triphenylchloromethane in toluene dropwise. After the addition was completed, the reaction was hold for 1 h, let it stand to separate the aqueous layer. The organic phase was cooled to 10° C., filtered and dried to obtain 46.0 g of N-triphenylmethyl-5-[4'-methylbiphenyl-2-yl]tetrazolium (formula I), with a yield of 93.0%; the purity of the compound of formula I in the product was 97.2%; the content of triphenylmethanol was 1.7%; the content of biphenyltetrazole was 0.5%; and the content of total impurities was 2.8%, as measured by HPLC.

Example 13

23.6 g of biphenyltetrazolium was dissolved in 100 mL of toluene, and added with sodium hydroxide aqueous solution. The mixture was stirred for 1 h, and added with 270 g of triphenylchloromethane in toluene recovered in Example 11 (containing 11.4% triphenylchloromethane) dropwise. After the addition was completed, the reaction was hold for 1 h, let it stand to separate the aqueous layer. The organic phase was concentrated under reduced pressure to remove 225 mL of toluene. The concentration was stopped and the concentrate was cooled to 10° C., filtered and dried to obtain 46.2 g of N-triphenylmethyl-5-[4'-methylbiphenyl-2-yl]tetrazolium (formula I), with a yield of 93.0%; the purity of the compound of formula I in the product was 97.2%; the content of triphenylmethanol was 1.7%; the content of biphenyltetrazole was 0.5%; and the content of total impurities was 2.8%, as measured by HPLC.

Comparative Example 1

30.7 g of triphenylchloromethane (purchased) was dissolved in 275 ml of toluene;
23.6 g of biphenyltetrazolium was dissolved in 100 mL of toluene, and added with sodium hydroxide aqueous solution. The mixture was stirred for 1 h, and added with triphenylchloromethane in toluene dropwise. After the addition was completed, the reaction was hold for 1 h, let it stand to separate the aqueous layer. The organic phase was concentrated under reduced pressure to remove 225 mL of toluene. The concentration was stopped and the concentrate was cooled to 10° C., filtered and dried to obtain 46.2 g of N-triphenylmethyl-5-[4'-methylbiphenyl-2-yl]tetrazolium (formula I), with a yield of 93.0%; the purity of the compound of formula I in the product was 97.0%; the content of triphenylmethanol was 1.8%; the content of biphenyltetrazole was 0.5%; and the content of total impurities was 3.0%, as measured by HPLC.

The data of Example 12, Example 13 and Comparative Example 1 were as follows:

| Examples | Triphenyl-chloromethane Source | Content % | Yield of product (formula I) % | Purity of product (formula I) % | Triphenyl-methanol content % | Biphenyl-tetrazolium content % | Total impurities content % | Conclusion |
|---|---|---|---|---|---|---|---|---|
| Example 12 | Example 1 | 99 | 93 | 97.2 | 1.7 | 0.5 | 2.8 | No obvious differences |
| Example 13 | Example 11 | 11.4 | 93 | 97.2 | 1.7 | 0.5 | 2.8 | |
| Comparative Example-1 | Purchased | 99 | 93 | 97.0 | 1.8 | 0.5 | 3.0 | |

The data results of the above Example 12, Example 13 and Comparative Example 1 show that no matter the intermediate N-triphenylmethyl-5-[4'-methylbiphenyl-2-yl]tetrazolium is synthesized by using purchased triphenylchloromethane or recovered triphenylchloromethane, there is no obvious difference in the yield or purity of the product.

The invention claimed is:

1. A method for preparing triphenylchloromethane, comprising the following steps:
adding a mixture of hydrochloric acid and Lewis acid to a mixture of triphenylmethanol and an organic solvent, reacting at 5-35° C. under stirring, separating a product from an organic phase after the reaction is completed to obtain a solid containing triphenylchloromethane; and obtaining triphenylchloromethane after drying; wherein the reaction scheme is as follows:

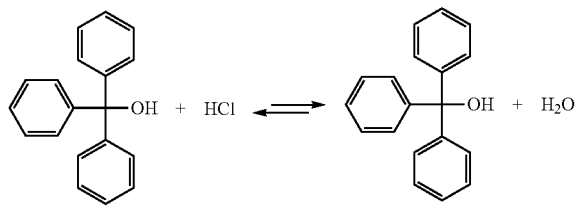 [SMILES: OC(c1ccccc1)(c1ccccc1)c1ccccc1 ; Cl ; OC(c1ccccc1)(c1ccccc1)c1ccccc1 ; O]

wherein the molar concentration of hydrochloric acid is 1-10 mol/L and
wherein the molar ratio of hydrochloric acid to Lewis acid is 1.1-1:0.01.

2. The method of claim 1, wherein Lewis acid is at least one of anhydrous calcium chloride, anhydrous aluminum chloride, anhydrous ferric chloride and anhydrous zinc chloride.

3. The method of claim 1, wherein the molar concentration of hydrochloric acid is 3-10 mol/L.

4. The method of claim 1, wherein the molar ratio of hydrochloric acid to triphenylmethanol is 15:1-1.5:1.

5. The method of claim 1, wherein the molar ratio of hydrochloric acid to Lewis acid is 1:0.1-1:0.01.

6. The method of claim 1, wherein the reaction temperature is 15-25° C.; and the reaction time is 0.5 to 10 hours.

7. The method of claim 1, wherein the organic solvent is at least one of tetrahydrofuran, 2-methyltetrahydrofuran, carbon disulfide, nitromethane, acetonitrile, chlorinated alkane, aromatic hydrocarbon, an ether solvent, an ester solvent and a ketone solvent.

8. The method of claim 7, wherein the chlorinated alkane is at least one of dichloromethane, chloroform, carbon tetrachloride, 1,1-dichloroethane, 1,2-dichloroethane, 1,1,1-trichloroethane, 1,1,2-trichloroethane and 1,1,2,2-tetrachloroethane; the aromatic hydrocarbon is at least one of toluene, chlorobenzene and nitrobenzene; the ether solvent is at least one of ethyl ether, propyl ether, isopropyl ether and butyl ether; the ester solvent is at least one of methyl acetate, ethyl acetate, propyl acetate, butyl acetate, isopropyl acetate, isobutyl acetate, pentyl acetate and isoamyl acetate; and the ketone solvent is at least one of acetone, butanone and methyl isobutyl ketone.

9. The method of claim 7, wherein the chlorinated alkane is dichloromethane.

10. The method of claim 7, wherein the aromatic hydrocarbon is toluene.

11. The method of claim 7, wherein the ether solvent is isopropyl ether.

12. The method of claim 1, wherein the drying is a vacuum drying; the drying temperature is 40-60° C.; and the drying time is 1-6 hours.

13. The method of claim 1, wherein the method further comprises recrystallizing the solid.

14. The method of claim 13, wherein a solvent for recrystallizing is at least one of petroleum ether, toluene, cyclohexane n-hexane, n-heptane, ethyl acetate, acetone and methyl isobutyl ketone.

15. The method of claim 1, wherein Lewis acid is anhydrous calcium chloride.

16. The method of claim 1, wherein the molar concentration of hydrochloric acid is 3-8 mol/L.

17. The method of claim 1, wherein the molar ratio of hydrochloric acid to triphenylmethanol is 10:1-1.5:1.

18. The method of claim 1, wherein the molar ratio of hydrochloric acid to Lewis acid is 1:1-1:0.1.

19. The method of claim 1, wherein the reaction time is 1 to 5 hours.

* * * * *

UNITED STATES PATENT AND TRADEMARK OFFICE
CERTIFICATE OF CORRECTION

PATENT NO. : 12,091,375 B2  
APPLICATION NO. : 17/616454  
DATED : September 17, 2024  
INVENTOR(S) : Zhang et al.

Page 1 of 1

It is certified that error appears in the above-identified patent and that said Letters Patent is hereby corrected as shown below:

In the Claims

In Column 11, Claim 1, Line 44, "1-10 moI/L and" should read -- 1-10 mol/L, and --.

In Column 11, Claim 1, Line 46, "1.1-1:0.01" should read -- 1:1-1:0.01 --.

In Column 12, Claim 14, Line 46, "cyclohexane n-hexane" should read -- cyclohexane, n-hexane --.

Signed and Sealed this  
Nineteenth Day of August, 2025

Coke Morgan Stewart  
*Acting Director of the United States Patent and Trademark Office*